US012635966B2

(12) United States Patent
Jaehn

(10) Patent No.: US 12,635,966 B2
(45) Date of Patent: May 26, 2026

(54) MANUFACTURING OF DENTAL IMPLANTS BASED ON DIGITAL SCAN DATA ALIGNMENT

(71) Applicant: INSTITUT STRAUMANN AG, Basel (CH)

(72) Inventor: Benjamin Jaehn, Chemnitz (DE)

(73) Assignee: INSTITUT STRAUMANN AG, Basel (CH)

( * ) Notice: Subject to any disclaimer, the term of this patent is extended or adjusted under 35 U.S.C. 154(b) by 317 days.

(21) Appl. No.: 18/317,949

(22) Filed: May 16, 2023

(65) Prior Publication Data

US 2023/0363732 A1    Nov. 16, 2023

(30) Foreign Application Priority Data

May 16, 2022    (EP) ..................................... 22173502

(51) Int. Cl.
  *A61B 6/00*        (2024.01)
  *A61B 6/03*        (2006.01)
       (Continued)

(52) U.S. Cl.
  CPC .............. *A61B 6/5235* (2013.01); *A61B 6/03* (2013.01); *A61C 9/0053* (2013.01); *G06T 7/11* (2017.01); *G06T 2207/30036* (2013.01)

(58) Field of Classification Search
  CPC ........... A61C 9/0053; A61C 8/00; G06T 7/11; G06T 2207/10081; G06T 17/00;
       (Continued)

(56) References Cited

U.S. PATENT DOCUMENTS 10,258,439 B1 *   4/2019   Kitching ................ A61C 7/002
2009/0316966 A1 *  12/2009   Marshall ................ G16H 50/30
                                                    382/128

(Continued)

FOREIGN PATENT DOCUMENTS

| CN | 108765474 A | 11/2018 | |
| CN | 112200843 A | 1/2021 | |
| WO | WO-2017143107 A1 * | 8/2017 | ........... A61C 8/0095 |

*Primary Examiner* — Vu Le
*Assistant Examiner* — Zaid Muhammad Saleh
(74) *Attorney, Agent, or Firm* — LEYDIG, VOIT & MAYER, LTD.

(57)                ABSTRACT

A process for aligning at least two different digital scan data each representing at least a part of a dentition of a patient includes scanning the patient's dentition so as to record volumetric 3-dimensional digital scan data in a volumetric coordinate system and scanning the patient's dentition so as to record topographic 3-dimensional digital scan data in a topographic coordinate system. The teeth or jaws of the patient's dentition are segmented and approximated from the digital scan data by grouping the digital scan data with respect to structures and approximating a surface of the segmented teeth using triangle meshes. A key point determination is performed for each tooth based on the triangle mesh representation to define 3-dimensional coordinates of a tooth surface feature in the volumetric or topographic coordinate system. The key points are aligned to obtain aligned digital scan data by coordinate transformation of one coordinate system.

13 Claims, 4 Drawing Sheets

(51) Int. Cl.
    *A61C 9/00*         (2006.01)
    *G06T 7/11*         (2017.01)

(58) Field of Classification Search
    CPC . G06T 2207/30036; G06T 2207/10088; G06T
               7/33; A61B 6/5235; A61B 6/03
    See application file for complete search history.

(56)                 References Cited

U.S. PATENT DOCUMENTS

2013/0282351 A1*   10/2013   Tank ....................... G06F 18/28
                                                  703/11
2021/0322136 A1*   10/2021   Anssari Moin ........ G16H 50/20

* cited by examiner

MANUFACTURING OF DENTAL IMPLANTS BASED ON DIGITAL SCAN DATA ALIGNMENT

CROSS REFERENCE TO RELATED APPLICATIONS

This application claims benefit to European Patent Application No. EP 22 173 502.0, filed on May 16, 2022, which is hereby incorporated by reference herein.

FIELD

The present invention relates to a process for the alignment of at least two different digital scan data each representing at least a part of the dentition of the same patient, wherein the different digital scan data are obtained by at least two different image recording methods.

BACKGROUND

The planning of a dental restoration and patient specific production of dental implants is a difficult task. On the one hand this finding is based on the fact, that especially in the field of dentistry each patient comprises a very specific teeth configuration. On the other hand the jaw and a single tooth can in rare cases be considered independently, only, because there is always an interrelation between different tooth positions in and between the yaws. Therefore, a complex treatment situation is present and has to be considered. In order to reduce the complexity for dental professionals, dental planning software is used to assist the planning of dental reconstruction of a patient's dentition and the production of patient specific solutions. The software may include the planning of the placement and the selection of dental implants, planning of orthodontic treatment plans, designing prosthetics (such as crowns, bridges, dentures, orthodontic aligners), and planning and designing surgical guides for use during implant installation and other dental surgery. To properly plan and design, the dental professional must be able to understand and work with an accurate representation of the patient's dentition, jaw(s) and other supporting structure. Imaging equipment such as Computed Tomography (CT) or Cone Beam Computed Tomography (CBCT) X-ray machines capture 3D images of jaws, teeth and provides detailed information that includes the dimensions and density of the jaw, teeth root locations, as well as nerve pathways. As an alternative or supplement, intra-oral scanners use optical technology to capture detailed colored surface information of the inside of a patient's mouth.

Such optical scanners can capture very high-resolution details of the visual topography of the dentition which, together with the CT data, can form the foundation of a planning and manufacturing process. The problem encountered in dental planning and manufacturing is the ability to obtain the best, combined information from both type of scans within a common, combined model. Both sensor data types (CBCT x-ray machine vs. intraoral optical scanner) are captured within a sensor specific three-dimensional coordinate system. To merge them together both scans must be aligned with each other. This process is usually referred as scan matching or registration and is, until now, very laborious and prone to errors, because the matching operation is either performed manually or in automated procedures only sub-optimal results are obtained.

The optimization of dental planning and manufacturing of dental devices is also disclosed in the patent literature.

CN 112 200 843A for instance discloses a method for tooth registration between CBCT and laser scanning point cloud data based on supervoxels. The method includes the following steps; First, extract the tooth model from the oral CBCT scan data according to the area growth method; Secondly, use a laser scanner to process the tooth model, and separate the crown in the tooth model from the abutment according to the characteristics of the teeth. Then the tooth models from different sources are converted into tooth point cloud data, and color information is added to the tooth point cloud data to assist in the initial geometric alignment of the tooth point cloud. At the same time, the point cloud is down-sampling based on the supervoxel method. Finally, combine the hybrid features of tooth point cloud data and define similarity measures accordingly, dynamically adjust the weight between the color and spatial information of tooth point cloud data, and finally measure the hybrid features of tooth point cloud data to construct an alignment metric; Mutual corresponding matching conditions based on mixed features. The registration method is an improved ICP registration algorithm under the ICP framework of the improved model. The components of the improved model include a point cloud embedding network, an attention-based module for approximate combination matching, and a pointer generation layer. Differentiable singular value decomposition layer for extracting the final rigid transformation; it can register two pieces of tooth point cloud data with color information from different angles.

Furthermore, CN 108 765 474 A describes a method comprising the steps of (1) data preparation in which 3D visualization is carried out on CT data of the oral cavity to obtain a CT reconstructed tooth image, visualization is carried out on optical scanning data of the tooth crown and gum part to obtain an optical scanning tooth crown image, and the CT reconstructed tooth image and the optical scanning tooth crown image are arranged in the unified world coordinate system; (2) initial registration in which characteristic points are selected manually to process the CT reconstructed tooth image and the optical scanning tooth crown image and further to obtain an initial registration model; and (3) accurate registration in which characteristic points are selected automatically to process the initial registration model and further to obtain an accurate registration model. Problems in registration data with scale transformation and different resolution are solved, and a registration result is high in convenience speed and low in registration error.

In addition, US 102 584 39 B1 discloses a method of manufacturing an orthodontic aligner or an orthodontic brace for a patient, the method comprising: determining, by a computational device, a representation of one or more anatomical features in an image that includes the patient's teeth; overlapping the image and a three-dimensional model of the patient's teeth in a three-dimensional space; correcting in an anatomically accurate manner, based at least in part on the determined representation of the one or more anatomical features, the orientation by which the three-dimensional model is viewed in the three-dimensional space; after correcting the orientation, measuring an orientation of an occlusal plane of the patient's teeth relative to the determined representation in the three-dimensional space; using the measured orientation to create a digital design for an orthodontic aligner or an orthodontic brace; and manufacturing the orthodontic aligner or the orthodontic brace based on the digital design.

Such solutions known from the prior art can still offer further potential for improvement, especially with regard to the reproducibility and quality of the alignment of the data of different scan sources and, consequently, the quality of the resulting orthodontic devices, generated from the data.

SUMMARY

In an embodiment, the present disclosure provides

A process for aligning at least two different digital scan data each representing at least a part of a dentition of the same patient, wherein the different digital scan data are obtained by at least two different image recording methods, comprising the process steps of:

a) scanning the patient's dentition with a volumetric image recording method so as to record volumetric 3-dimensional digital scan data in a volumetric coordinate system;

b) scanning the patient's dentition with a topographic image recording method so as to record topographic 3-dimensional digital scan data in a topographic coordinate system;

c) segmenting and approximating the teeth and/or jaws of the patient's dentition from the digital scan data, wherein the segmenting is performed on the teeth in the volumetric and topographic coordinate system and comprises the steps:

c1) segmenting the digital scan data, wherein the digital scan data are grouped with respect to the single tooth and/or jaw structures;

c2) approximating a surface of the segmented teeth and/or jaws using triangle meshes, wherein an individual representation of the teeth and/or jaw surface in the form of connected triangle meshes is obtained;

d) performing a key point determination for each tooth, wherein the key point determination is based on the triangle mesh representation of each tooth and defines 3-dimensional coordinates of a tooth surface feature in the volumetric or topographic coordinate system, respectively;

e) aligning the key points obtained in step d) in order to obtain aligned digital scan data, wherein the alignment between the data of the volumetric coordinate system and the data of the topographic coordinate system is performed by a coordinate transformation of one coordinate system and the coordinate transformation is based at least on the 3-dimensional coordinates of the key points in the volumetric and topographic coordinate system.

BRIEF DESCRIPTION OF THE DRAWINGS

Subject matter of the present disclosure will be described in even greater detail below based on the exemplary figures. All features described and/or illustrated herein can be used alone or combined in different combinations. The features and advantages of various embodiments will become apparent by reading the following detailed description with reference to the attached drawings, which illustrate the following.

DETAILED DESCRIPTION

Figure 1:
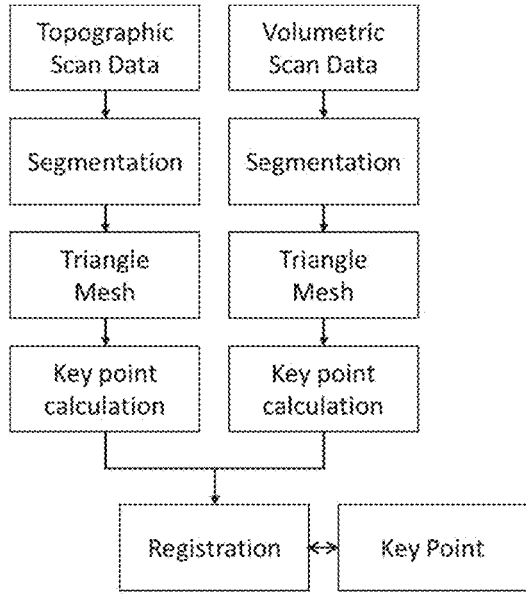
FIG. 1 a schematic representation of the process according to the invention.

In an embodiment, the present disclosure at least partially overcomes the disadvantages known from the prior art. In particular, it is the present invention provides an improved process, which enables a reliable, faster and less error prone registration of different scan data and, therefore, the production of improved dental devices, e.g., in the form of surgical guides.

Preferred embodiments of the invention are indicated in the description or in the figures, whereby further features described or shown in the description or in the figures may individually or in any combination constitute an object of the invention, unless the opposite clearly follows from the context.

According to at least one embodiment, the present invention provide a process for the alignment of at least two different digital scan data each representing at least a part of the dentition of the same patient, wherein the different digital scan data are obtained by at least two different image recording methods. The process at least comprises the process steps of:

a) Recording volumetric 3-dimensional digital scan data in a volumetric coordinate system by scanning the patient's dentition with a volumetric image recording method;

b) Recording topographic 3-dimensional digital scan data in a topographic coordinate system by scanning the patient's dentition with a topographic image recording method;

c) Segmentation and approximation of the teeth and/or jaws of the patient's dentition from the digital scan data, wherein the segmentation is performed on the teeth in the volumetric and topographic coordinate system and comprises the steps:

c1) Segmentation of the digital scan data, wherein in the segmentation the digital scan data are grouped with respect to the single tooth and/or jaw structures;

c2) Approximation of the surface of the segmented teeth and/or jaws by triangle meshes, wherein an individual representation of the teeth and/or jaw surface in the form of connected triangle meshes is obtained;

d) Key point determination for each tooth, wherein the key point determination is based on the triangle mesh representation of each tooth and defines the 3-dimensional coordinates of a tooth surface feature in the volumetric or topographic coordinate system, respectively;

e) Alignment of the key points obtained in step d) in order to obtain aligned digital scan data, wherein the alignment between the data of the volumetric coordinate system and the data of the topographic coordinate system is performed by a coordinate transformation of one coordinate system and the coordinate transformation is based at least on the 3-dimensional coordinates of the key points in the volumetric and topographic coordinate system.

The above-described process is able to provide an accurate alignment or registration of digital scan data of different scan sources in an automated and user independent way. Based on the fact that each digital representation of a patient's dentition is provided by the scan method in its own coordinate system, it is not possible to combine digital representations of different methods as such. The digital representations have to be aligned in order to provide the same perspective on the patient's dentition. The situation gets even more complicated in cases, wherein the different scan methods provide a different "picture" of the same oral situation. This is for instance the case if different scan methods are used, wherein e.g. one method provides 3-dimensional volume data of the oral cavity including teeth and jaws. If further scan methods are available, but these methods provide, for instance, "only" three-dimensional representations of the oral cavity surface, it becomes even more difficult to match the data, based on the different information content of both scans. It has been found, that the inventive process is especially able to align data sources of such different origin comprising different coordinate systems of the data representations, wherein a more reproducible and better alignment is achieved compared to manual or semi-automatic registration routines within a fraction of time. Based on the alignment it is possible to provide a unified and more detailed comprehensive view of the teeth and jaws of the patient at hand, wherein this view can, generally, be used to provide a more intuitive and accurate planning of oral procedures. Besides this planning it is especially possible to provide more precise data from the matched data for manufacturing of patient specific adapted dental devices. The devices can be tailored to the detailed situation and can provide a better fitting solution compared to a planning or manufacturing of devices based on non-matched or only semi-optimal matched or aligned data.

The inventive process is a process for the alignment of at least two different digital scan data each representing at least a part of the dentition of the same patient, wherein the different digital scan data are obtained by at least two different image recording methods. Different intra-oral scanning methods deliver method specific data, wherein the perspective to the teeth and the oral cavity depends on the measuring device and in certain cases also on the operator. Between different methods no direct correlation between the different views and perspectives is known and, therefore, digital representations cannot just be combined in order to result in a common picture, providing all the information from both views. An alignment or registration enables a combined view, wherein the different data are matched in origin and orientation and enables a combined view of the dentition. The different methods can be applied at different time points, but, of course, have to provide a digital representation of at least a shared sub-group of the same teeth and/or jaws of the same patient. Different image recording methods provide data based on a different physical process. Therefore, the recording methods might be grouped as a function of the applied physical means, e.g. visible light, X-rays, IR, magnetic or electric spin etc.

The process comprises the process step a), wherein volumetric 3-dimensional digital scan data in a volumetric coordinate system are recorded by scanning the patient's dentition with a volumetric image recording method. Volumetric 3-dimensional digital scan data originate from a scan method which is able to provide not only surface, but volume information of the dentition at hand. Methods like CBCT or MRT are able to provide density related data, wherein volume structures like a tooth or a jaw can be assessed not only on the surface, but the overall structure comprising the same or a similar density is resolved. Scanning of a patient's dentition means that at least a part of the oral cavity including tooth and/or jaw structures are scanned and the data is recorded.

The process comprises the process step b), wherein topographic 3-dimensional digital scan data in a topographic coordinate system are recorded by scanning the patient's dentition with a topographic image recording method. Topographic 3-dimensional digital scan data originate from a scan method which is able to provide surface, but no volume information of the dentition at hand. E.g. optical methods using light as the probe are able to provide colored surface related data with high resolution and accuracy, but no volume structures below the surface can be assessed. Intra oral scanners for instance provide a 3-dimensional representation of the surface of a patient's dentition including the gum and jaw surface structures. In contrast to typical volumetric scan methods, especially soft tissue structures can be detected.

In step c) a segmentation and approximation of the teeth and/or jaws of the patient's dentition from the digital scan data is done, wherein the segmentation is performed on the teeth in the volumetric and topographic coordinate system. Both recording methods deliver digital representations of the oral cavity including teeth and jaws. These data are processed in this step, in order to separate the structures of interest, like a single tooth or jaw, from the overall scan of the dentition. This process is performed independently for both scan data sets and results in two sets of data, where the volumetric as well as the topographic 3-dimensional digital scan data comprises information about separated single structures in the oral cavity. The separation in this context means, that a further processing of the data concerning single structures, e.g. a tooth, in the oral cavity is possible. The data representing the single structures are restructured and approximated, for instance in order to reduce the overall data amount.

The segmentation step c) comprises the sub-step c1), wherein a segmentation of the digital scan data is performed, wherein in the segmentation the digital scan data are grouped with respect to the single tooth and/or jaw structures. The segmentation of the digital scan data of each method can be performed by methods known to the skilled artisan either manually or (semi-) automated. As explained above, in the segmentation the overall data are splitted in separated groups, wherein each different group represent a single labeled structure of the overall oral cavity. The label reflects the type and, where applicable, the position of the structure, e.g. a specific tooth or either upper/lower jawbone. These separated structures can be further processed and handled individually.

The segmentation step c) also comprises the sub-step c2), wherein an approximation of the surface of the segmented teeth and/or jaws by triangle meshes is performed, wherein an individual representation of the teeth and/or jaw surface in the form of connected triangle meshes is obtained. In order to reduce the complexity of the system and the amount of data it has been found useful, to transform the separated structures to a triangle mesh representation. A mesh representation of surface structures is known in the field of dentistry and the transformation as such is known to the skilled artisan. The transformation is performed on each segmented individual structure of the volumetric 3-dimensional digital scan data and the topographic 3-dimensional digital scan data. It is also possible that the scanning method calculates and returns such mesh representation by itself during the scanning process. In such cases a separate, additional transformation is of course not necessary.

In step d) a key point determination for each tooth is performed, wherein the key point determination is based on the triangle mesh representation of each tooth and defines the 3-dimensional coordinates of a tooth surface feature in the volumetric or topographic coordinate system, respectively. A tooth key point is a significant and visible structure on the outer surface of a tooth. Possible key points may by chosen for convenience and might include the circumference of a tooth at a specific high, the mid-point of a tooth upper surface, an edge position of a tooth or the like. These tooth key points are determined for each of the segmented tooth in the volumetric and topographic model. The key point can be represented by the three-dimensional coordinates of that structure for the specific tooth. Based on the fact that for all teeth a key point is determined, the location of the key point on the single tooth and the three-dimensional interrelation between all teeth in the given model is obtained.

In step e) an alignment of the key points obtained in step d) is performed in order to obtain aligned digital scan data, wherein the alignment between the data of the volumetric coordinate system and the data of the topographic coordinate system is performed by a coordinate transformation of one coordinate system and the coordinate transformation is based at least on the 3-dimensional coordinates of the key points in the volumetric and topographic coordinate system. Based on the correspondences of the tooth key points belonging to the same tooth in each model, it is possible to derive a mathematical transformation as such that both key point sets match. The correspondences could be established by the tooth specific position label from step c1). The transformation of the key points of one of the models may for instance include a translatory and/or rotatory transformation for the complete set of key points of one scan method. The translatory and/or rotatory transformation of one set of key points results in a representation, wherein the key points of both data set comprise the same or similar three-dimensional coordinates. This transformation is the basis, that both scan methods can be represented within the same coordinate system and that a more detailed and more comprehensive picture is obtained. Based on the combined model a better planning of dental applications and a patient specific manufacturing of dental devices can be performed.

Within a preferred aspect of the process, within or after step c) and before step e) a jaw position sensitive label of a dental notation coordinate system can be assigned to each tooth in the volumetric and the topographic scan and the alignment in step e) may further include a comparison of the match of the jaw position sensitive labels of the teeth in the volumetric and the topographic coordinate system. In step c) or d) the segmented teeth can be labeled according to any dental notation coordination system. In such system usually a specific descriptor is attached to a tooth as a function of the tooth position within the jaw. A possible, known notation is the FDI notation as described below. Nevertheless, it is also possible to use arbitrary notation systems, wherein different but unique descriptors per tooth may be used. Both segmented teeth in the volumetric and the topographic data set are separately augmented with such a label and the alignment of the two sets is also performed as a function based on the correspondences of the teeth labels of both sets. Such process can accelerate the matching procedure between both coordinate systems and may further improve the repeatability also in cases wherein difficult jaw or teeth constellations in the form of bridges or several missing teeth are present. Especially in this case a more reliable assignment can be achieved.

In a preferred embodiment of the process, the comparison of the assigned position sensitive labels is included in the step e) prior to the alignment of the key points in the volumetric and topographic coordinate system. For the fastness and robustness of the overall process it has been found favorable, that label comparison between the teeth of both coordinate systems is performed prior to the key point alignment. Such comparison is especially effective in case that one or more teeth are missing in just one data set or in case that complex crowns or bridge structures are present. Thus, just key points for teeth which are available in both scan data sets were used for the key point alignment which increases the robustness and reduces the complexity.

Within a preferred characteristic of the process, the comparison of the label match can be based on the residual error in the form of the sum of the squared distances between corresponding tooth positions and the comparison can be performed multiple times, wherein several different sets of labels are generated, wherein the sets differ at least in the assignment of at least one tooth label. The key point correspondences based on the assigned labels during step c2) can be very helpful to achieve a good registration result. The quality of this registration can be rated as a function of the residual error in the form of the sum of the squared distances between corresponding tooth key point positions after the transformation is applied. This procedure can be performed multiple times, wherein several different sets of suitable label error assumptions, and thus different correspondence assignments, will be used to increase the robustness to labeling errors. The final key point registration result is the one with the smallest residual error. Such step can be necessary especially in cases, wherein the teeth position label from step c2) is erroneous, presumably resulting in inconsistent labels for the different data sets. Especially in case of tooth gaps or dental bridges the labeling procedures could lead to, usually small, position offsets. If a tooth gap is detected just within one data set and not in the other, wrong correspondences will be established and thus the registration result will be not optimal. Applying the registration to all possible key point combinations between the two data sets and comparing the results would be a computational costly and time-consuming task. Thus, checking suitable, e.g. random subsets, close to the original correspondence assignment matrix, limits the amount of combinations to a manageable set. Such a random label offsetting scheme may help to find better matching solutions. Based on the comparison on the basis of the segmented teeth, this comparison and matching can be performed rather fast and accelerates the following comparison step based on the mesh representation.

According to a preferred embodiment of the process, the difference in the label can be set to one position. The amount of alternative label correspondence assignments can be reduced further by applying the following scheme. Considering the assumption that if a certain tooth position label is wrong, the neighboring teeth will be also shifted on the same amount. This increment can reduce the number of combinations to an easily manageable size. If a certain tooth position in the labeling scheme is free, all succeeding possible continuous subsets will be shifted by one and, thus, a much smaller set of labeling hypotheses is derived, wherein the corresponding registration results could be derived and compared within a reasonable amount of processing time. This further comparison may help to identify any false label classification in the prior label assignment step.

In a further preferred embodiment of the process, FDI (World Dental Federation notation) labels according to ISO 3950 "Dentistry-Designation system for teeth and areas of the oral cavity" are assigned to each tooth in the volumetric and the topographic coordinate system. For a fast and reliable processing also for difficult teeth set-ups it has been found useful, that the FDI system for tooth labeling and, consequently, the comparison of this labels is used. Based on the symmetry of this notation it is easy to derive comparable results in both scan sets. Nevertheless any consistent naming scheme would applicable as well.

According to a further preferred embodiment of the process, in the key point determination in step d) the crown peak point of each tooth can be determined. For a reliable matching based on the key points the crown peak point of every tooth has been found useful for comparison and matching. This key point is, compared to other structures, rather small and is usually very well captured by the different scanning methods. The crown peak point of a tooth is defined as the highest, lowest for upper jawbone teeth, extension of that tooth into the oral cavity.

In a preferred aspect of the process, the volumetric 3-dimensional digital scan data can be obtained by a method selected from the group consisting of Computed Tomography (CT), Cone Beam Computed Tomography (CBCT) or magnetic resonance tomography (MRT). The inventive process has been found especially useful for registration of volumetric data obtained by the above-described group of methods. The registration or matching between the different methods can be performed very reliable and the registration results in a better combined view, wherein this better view is the basis of a more precise planning and device manufacturing process.

According to a further preferred embodiment of the process, the topographic 3-dimensional digital scan data can be obtained by an optical intra oral scanner. The inventive process has been found especially useful for registration of topographic data obtained by an optical scanner. The registration or matching between the oral scanner data and the volumetric 3-dimensional digital scan data can be performed very reliable and the registration results in a better combined or registered view, wherein this better view is the basis of more precise planning and device manufacturing.

In a preferred aspect of the process, the alignment in step e) can be performed in a two-step procedure, wherein in a first, coarse alignment a first coordinate transformation is performed based on the key points 3-dimensional position in the volumetric and the topographic coordinate system and in a second, fine alignment a second coordinate transformation is performed based on a comparison of the triangle mesh representations of the teeth in the volumetric and the topographic coordinate system. For the performance of the overall system and for the reliability to find the right registration between the different coordinate systems it has been found useful to split the overall alignment in two steps. The first step is performed by the guidance of the key points and usually results in a fairly good alignment between the coordinate systems. In case that the highest precision in matching is needed the fine alignment can be performed on the already found position. The fine alignment is more time consuming, because this step is based on a comparison of the triangle mesh data and these data group is much larger compared to the key points. Furthermore, this step-wise approach may also be useful in very difficult cases, wherein one or more tooth are missing either on different places or consecutively in a jaw.

According to a preferred embodiment of the process, the coarse alignment can be based on an optimization of the sum of the squared distances between corresponding key points in the volumetric and the topographic coordinate system. For a fast and reproducible alignment it has been found useful to use the sum of the squared distances between corresponding key points as the alignment optimization target function. Minimizing this function results in the required transformation parameters. The calculation can be very fast and the mathematical model allows an optimal intermediate result, which can be processed further in the fine registration.

According to a further preferred embodiment of the process, the fine alignment step can be based on an Iterative Closest Point (ICP) algorithm. To increase the alignment precision further a specific version of the Iterative Closest Point (ICP) algorithm can be used. The objective of that algorithm is to align two point-clouds of the same object with each other. It does so by first finding point correspondences between the two clouds and second finding a transformation (three-dimensional rotation and translation) which minimizes a certain metric, in the simplest case also the sum of the squared distances (so called point-to-point metric), between the correspondences. The transformation is applied to the first point cloud and these two steps are repeated until a convergence criterion is reached, and the algorithm returns the final accumulated transformation matrix. The vertices of the two triangle mesh data sets of, for instance, a CBCT scanner and an optical intraoral scanner could be interpreted as two pointclouds from the same jaw. Due to the available triangle information within each mesh the surface normals for each vertice can be calculated. Thus, a more effective computational "point-to-plane" metric can be applied during the transformation optimization step. Therefore, the sum of the squared distances between each vertice point and its corresponding surface defined by the point and normal of the other point cloud is minimized.

Based on the fact that separated meshes for each tooth are already calculated, the possible point combinations to points from the same corresponding tooth from the other scan during the correspondence matching step can be limited. This results in a computational effective, robust, and accurate registration result.

Furthermore, according to the invention is the use of the process according to the invention in the manufacturing of a dental reconstruction of a patient's dentition. Based on the better registration of the scan data from the different sources as described above it is possible to provide a better planning of dental treatments and it is possible to adapt the design and manufacturing of any devices used in the course of a treatment or for a dental reconstruction with respect to the specific patient's needs. Failures in the treatment are avoided and as a result of the better fit of the devices less treatment problems and in certain cases an accelerated healing can be achieved.

Within a preferred embodiment of the use, the dental reconstruction can be selected from the group consisting of dental implants, prosthetics selected from the group consisting of crowns, bridges, dentures, orthodontic aligners; surgical guides for use during implant installation or combinations of at least two members of the group. Especially the members of said group of dental reconstruction devices can benefit from the improved process according to the invention. The reconstructions can be adapted very precisely to the patient's need and any misconstructions or special incompatibilities are avoided.

In addition, a dental reconstruction device is within the scope of this invention, wherein the device is manufactured including a device design step based on the inventive process. For the advantages of a device, it is especially referred to the advantages of the inventive process and the advantages of the inventive use.

Furthermore, according to the invention is a computer program product comprising computer readable program code for performing the process according to the invention.

FIG. 1 displays the different steps of the inventive process. In a first stage the volumetric 3-dimensional digital scan data and the topographic 3-dimensional digital scan data are processed separately. Each scan data set is segmented and after segmentation the single structures in the oral cavity like teeth or yaws are resolved and can be handled separately. For each segmented structure a triangle mesh representation of the surface structures is generated. It may be the case, that the scan data are already present also in a mesh representation. In such case the triangle mesh transformation step can be skipped. Based on the triangle mesh representation of the teeth surface structures the key points of each tooth can be detected. A possible key point may be the crown peak point of each tooth. The registration, i.e. the alignment of both scan coordinate systems, is performed based on the 3-dimensional position of the key points. For the alignment for instance the sum of the squared distance between corresponding teeth in the different scan coordinate systems can be used as a quality parameter. Within the optimization process a translatory and rotatory transformation is achieved. Based on the registration a combined picture is available, representing the details of the topographic 3-dimensional digital scan data and the volumetric 3-dimensional digital scan data in a common view. Based on the matched data-set a better planning and production of dental devices is possible.

Figure 2:
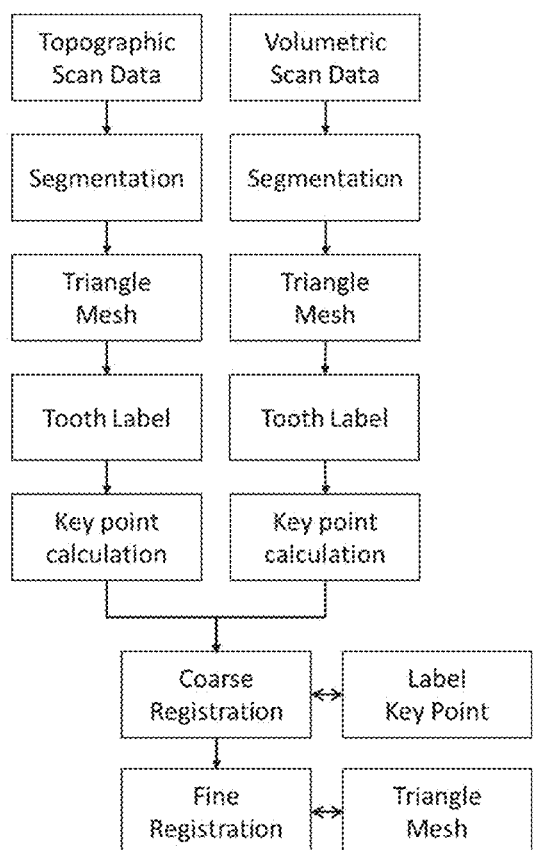
FIG. 2 a schematic representation of the process according to the invention.

FIG. 2 shows a preferred embodiment of the inventive process. In a first stage the volumetric 3-dimensional digital scan data and the topographic 3-dimensional digital scan data are processed separately. Each digital scan data set is segmented and after segmentation the single structures in the oral cavity like teeth or yaws are resolved and can be handled separately. For each segmented structure a triangle mesh representation of the surface structures is generated. It may be the case, that the scan data are already present also in a mesh representation. In such case the triangle mesh transformation step can be skipped. Based on the triangle mesh representation of the teeth surface structures the key points of each tooth can be detected. A possible key point may be the crown peak point of each tooth. Besides the key point determination also a label is attached to all teeth, wherein the label is a function of the tooth position in the yaw. A possible label may be an FDI label. The label attachment can be performed before or after key point calculation. The registration step, i.e. the alignment of both scan coordinate systems, is performed stepwise. In a first, coarse registration step the two coordinate systems are aligned based on the labels and the key points. The alignment as a function of the tooth label may further be repeated several times, wherein different labels may be attached to at least one tooth of all teeth in that coordinate system. This step might detect any wrong tooth labels and may result in a better matching. After the alignment is performed as a function of the label correspondences and key points the registration can further be optimized by considering the whole meshes of the individual teeth instead of the key points, only. Within that second step of the registration both coordinate systems can further be aligned based on the triangle mesh representation of the surface structures. In this step the overall transformation between the two coordinate systems is much smaller compared to the coarse registration step. Nevertheless, within this step an "optimum" in alignment between both coordinate systems can be achieved. Based on the registration a combined and precise picture is available, representing the details of the topographic 3-dimensional digital scan data and the volumetric 3-dimensional digital scan data. Within the optimization process a translatory and rotatory transformation is achieved. Based on the matched data-sets a better planning and production of dental devices is possible.

Figure 3:
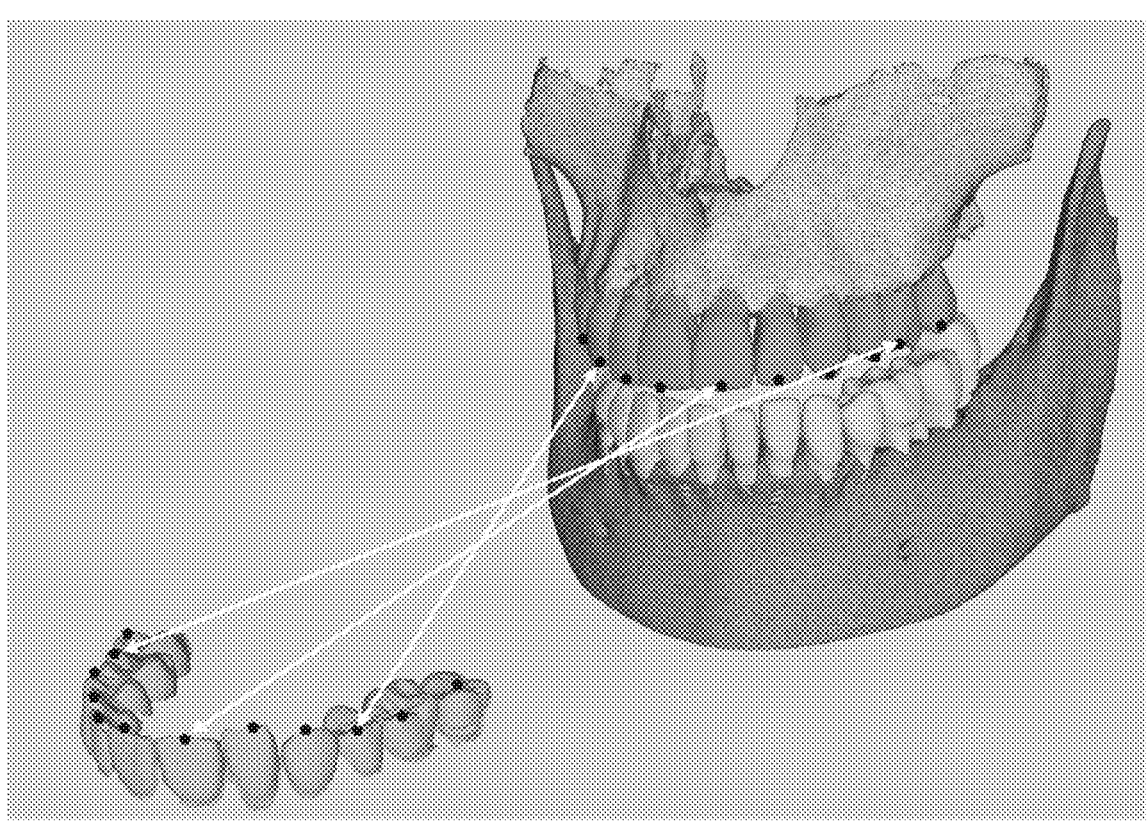
FIG. 3 a registration of CBCT data and an optical scan based on key points.

FIG. 3 shows an example of topographic 3-dimensional digital scan data obtained from the surface of patient's teeth and volumetric 3-dimensional digital scan data in the form of a three-dimensional representation of the surface and the internal structure of jaws and teeth. Both representations are independent from another and within the inventive process the surface data, e.g. from an intra-oral scanner, are matched with the volumetric data of a CBCT scan. The registration derives a transformation in order to combine both data sets.

Figure 4:
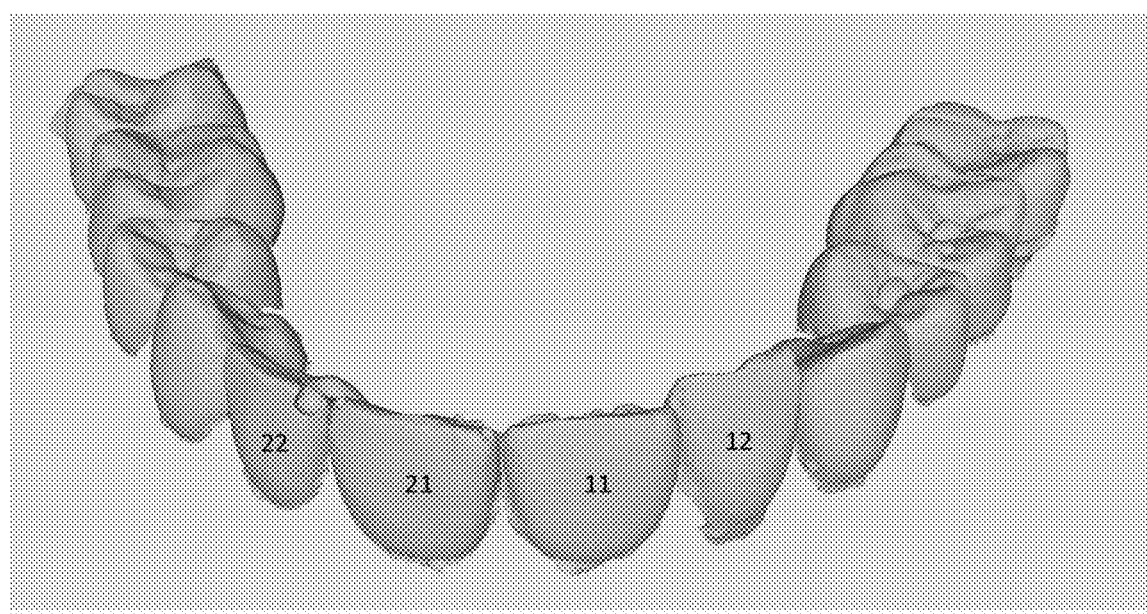
FIG. 4 an exemplary a labeling scheme according to FDI.

FIG. 4 displays a possible tooth labelling scheme. In the labelling step each tooth is assigned using a label according to the FDI notation. In case that the label position is changed in optimization, the label of at least one tooth is changed. In this figure it is possible that the label of tooth 12 is changed to 13, probing the possibility that in the labeling step a wrong label was attached. Such labelling change is very helpful in cases where a tooth or teeth are missing.

Figure 5:
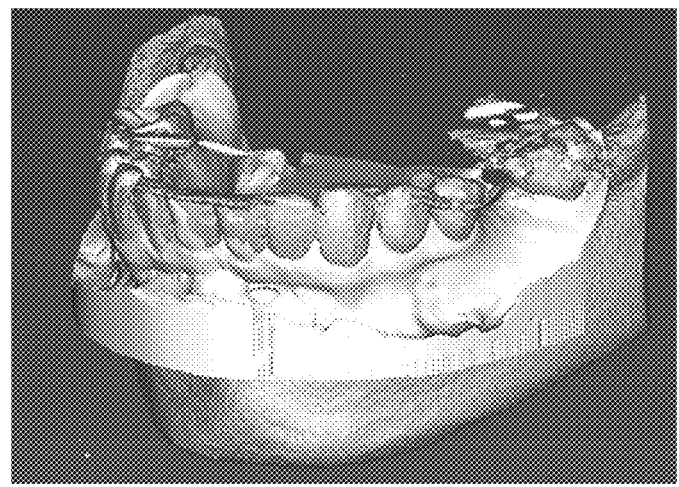
FIG. 5 an example of a combined 3D view of a CBCT and optical scan.

FIG. 5 displays a three-dimensional visualization of the aligned data. The optical scan is shown as the bright smooth structure above the darker rough structure of the CBCT scan. Especially the soft tissue structures were not present within the CBCT scan and thus the optical scan extends the information content of the view and thus enables better planning capabilities.

Figure 6:
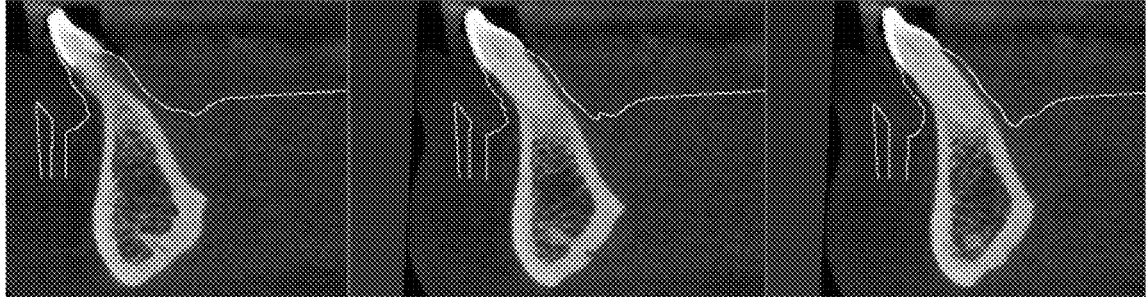
FIG. 6 an example of a combined cut view of a CBCT and optical scan.

FIG. 6 shows a cut view of the aligned data. The small white polyline represents the optical scan. Relative to the structures with high density it again shows the extent of the soft tissue structures like the gum.

Figure 7:
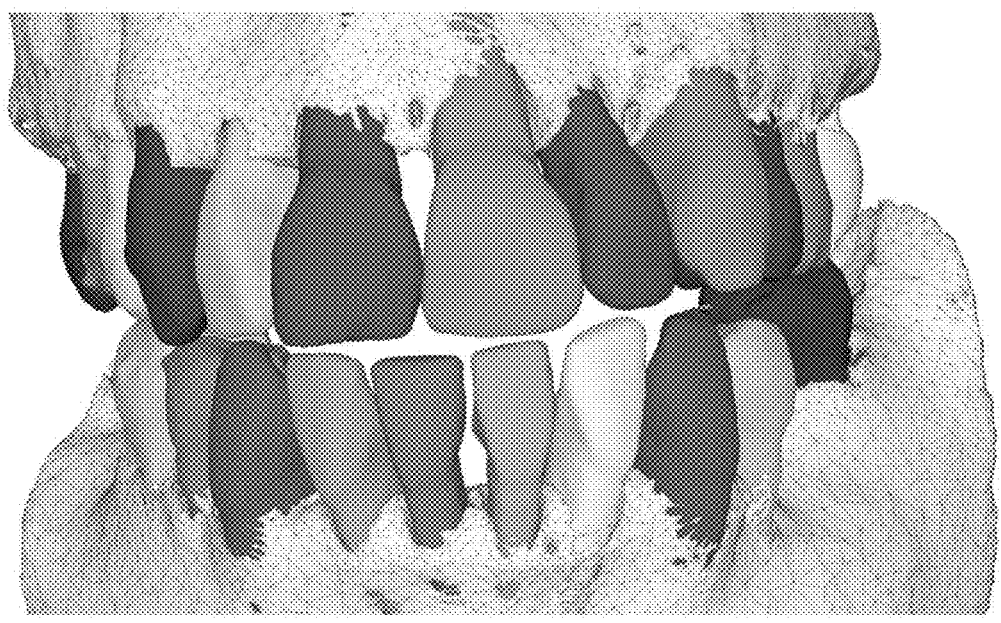
FIG. 7 an example of segmented and separated teeth meshes of a CBCT scan.

FIG. 7 shows the segmentation result of a CBCT scan which have been converted to triangle meshes. Each tooth is separated from the jawbone and can be further processed individually. This, together in certain cases with an assigned position label is the foundation for the registration process.

Figure 8:
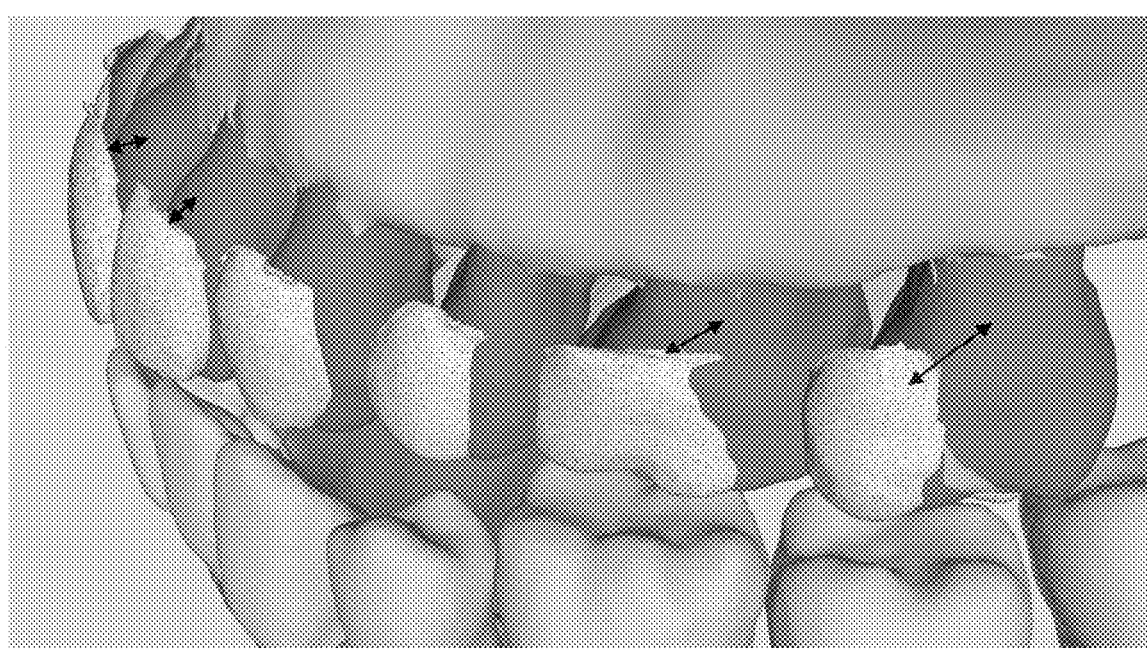
FIG. 8 an example of results after key point-based registration.

FIG. 8 shows the result of the key point based registration. The optical scan, shown as structured white mesh, is already quite close to the meshes from the upper jawbone of the CBCT scan, shown as solid in darker gray. Nevertheless, the registration result is not perfect as the black double-sided arrows indicate. There is still a gap between the two scan data sets. This may appear in cases, wherein there is a mismatch in the assignment of the key point positions between both data sets.

Figure 9:
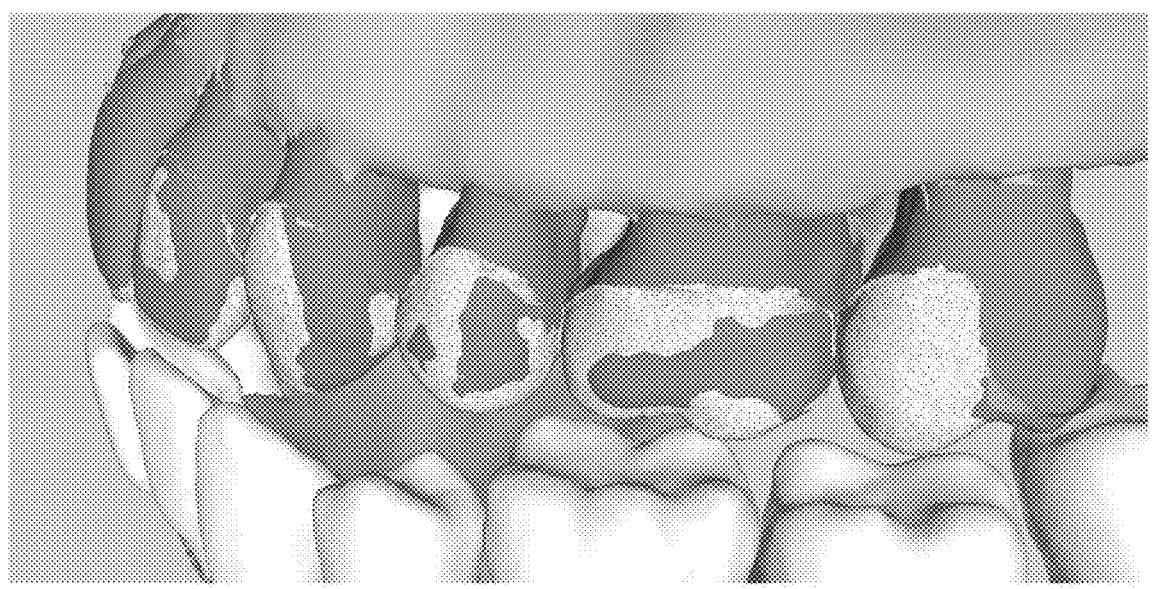
FIG. 9 an example of a results after fine registration.

FIG. 9 shows the result of the fine registration. The optical scan, shown as structured white mesh, fits perfectly on the upper jawbone teeth meshes from the CBCT scan shown in dark gray. Due to the different scanning procedures and the different processing and approximation processes both data sets are not congruent. But the alignment result is precise enough to view both complete data sets in a common view and enables an impression of the soft tissue structures relative to the structures with higher density like bones and teeth.

While subject matter of the present disclosure has been illustrated and described in detail in the drawings and foregoing description, such illustration and description are to be considered illustrative or exemplary and not restrictive. Any statement made herein characterizing the invention is also to be considered illustrative or exemplary and not restrictive as the invention is defined by the claims. It will be understood that changes and modifications may be made, by those of ordinary skill in the art, within the scope of the following claims, which may include any combination of features from different embodiments described above.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A process for aligning at least two different digital scan data each representing at least a part of a dentition of the same patient, wherein the different digital scan data are obtained by at least two different image recording methods, comprising the process steps of:
   a) scanning the patient's dentition with a volumetric image recording method so as to record volumetric 3-dimensional digital scan data in a volumetric coordinate system:
   b) scanning the patient's dentition with a topographic image recording method so as to record topographic 3-dimensional digital scan data in a topographic coordinate system:
   c) segmenting and approximating the teeth and/or jaws of the patient's dentition from the digital scan data, wherein the segmenting is performed on the teeth in the volumetric and topographic coordinate system and comprises the steps:
   c1) segmenting the digital scan data, wherein the digital scan data are grouped with respect to the single tooth and/or jaw structures:
   c2) approximating a surface of the segmented teeth and/or jaws using triangle meshes, wherein an individual representation of the teeth and/or jaw surface in the form of connected triangle meshes is obtained:
   d) performing a key point determination for each tooth, wherein the key point determination is based on the triangle mesh representation of each tooth and defines 3-dimensional coordinates of a tooth surface feature in the volumetric or topographic coordinate system, respectively:
   e) aligning the key points obtained in step d) in order to obtain aligned digital scan data, wherein the alignment between the data of the volumetric coordinate system and the data of the topographic coordinate system is performed by a coordinate transformation of one coordinate system and the coordinate transformation is based at least on the 3-dimensional coordinates of the key points in the volumetric and topographic coordinate system,
wherein within or after step c) and before step e) a jaw position sensitive label of a dental notation coordinate system is assigned to each tooth in the volumetric and the topographic scan and the alignment in step e) further includes a comparison of the match of the jaw position sensitive labels of the teeth in the volumetric and the topographic coordinate system, and
wherein the comparison of the assigned position sensitive labels is included in the step e) prior to the alignment of the key points in the volumetric and topographic coordinate system.

2. The process according to claim 1, wherein FDI labels according to ISO 3950 "Dentistry—Designation system for teeth and areas of the oral cavity" are assigned to each tooth in the volumetric and the topographic coordinate system.

3. The process according to claim 2, wherein the comparison of the label match is based on the residual error in the form of the sum of the squared distances between corresponding tooth positions and the comparison is performed multiple times, wherein several different sets of labels are generated, wherein the sets differ at least in the assignment of at least one tooth label.

4. The process according to claim 3, wherein the difference in the label is set to one position.

5. The process according to claim 1, wherein in the key point determination in step d) the crown peak point of each tooth is determined.

6. The process according to claim 1, wherein the volumetric 3-dimensional digital scan data are obtained by a method selected from the group consisting of Computed Tomography, Cone Beam Computed Tomography or magnetic resonance tomography.

7. The process according to claim 1, wherein the topographic 3-dimensional digital scan data are obtained by an optical intra oral scanner.

8. The process according to claim 1, wherein the alignment in step e) is performed in a two-step procedure, wherein in a first, coarse alignment a first coordinate transformation is performed based on the key points 3-dimensional position in the volumetric and the topographic coordinate system and in a second, fine alignment a second coordinate transformation is performed based on a comparison of the triangle mesh representations of the teeth in the volumetric and the topographic coordinate system.

9. The process according to claim 8, wherein the coarse alignment is based on an optimization of the sum of the squared distances between corresponding key points in the volumetric and the topographic coordinate system.

10. The process according to claim 8, wherein the fine alignment step is based on an Iterative Closest Point algorithm.

11. The process according to claim 1 further comprising manufacturing a dental reconstruction of a patient's dentition.

12. The process according to claim 11, wherein the dental reconstruction is selected from the group consisting of dental implants, prosthetics selected from the group consisting of crowns, bridges, dentures, orthodontic aligners: surgical guides for use during implant installation or combinations of at least two members of the group.

13. A non-transitory computer-readable medium having processor-executable instructions stored thereon, wherein the processor-executable instructions, when executed by one or more processors, facilitate performance of the method of claim 1.

\* \* \* \* \*